(12) United States Patent
Marques-Smith et al.

(10) Patent No.: US 12,721,564 B2
(45) Date of Patent: Sep. 1, 2026

(54) WEARABLE SENSOR

(71) Applicant: OCCAM BCI, INC., Middletown, DE (US)

(72) Inventors: André Filipe Marques-Smith, Almada (PT); Ana Montero Horas, Almada (PT)

(73) Assignee: OCCAM BCI, INC., Middletown, DE (US)

( * ) Notice: Subject to any disclaimer, the term of this patent is extended or adjusted under 35 U.S.C. 154(b) by 583 days.

(21) Appl. No.: 17/982,706

(22) Filed: Nov. 8, 2022

(65) Prior Publication Data

US 2023/0148932 A1 May 18, 2023

(30) Foreign Application Priority Data

Nov. 15, 2021 (GB) ...................................... 2116428

(51) Int. Cl.

| | |
|---|---|
| ***A61B 5/291*** | (2021.01) |
| ***A61B 5/00*** | (2006.01) |
| ***A61B 5/257*** | (2021.01) |

(52) U.S. Cl.

CPC ............ *A61B 5/291* (2021.01); *A61B 5/0006* (2013.01); *A61B 5/257* (2021.01); *A61B 5/6833* (2013.01); *A61B 2560/0214* (2013.01); *A61B 2562/166* (2013.01)

(58) Field of Classification Search

CPC ....... A61B 5/291; A61B 5/0006; A61B 5/257; A61B 5/6833; A61B 2560/0214; A61B 2562/166; A61B 2562/164; A61B 5/01; A61B 5/0205; A61B 5/02055; A61B 5/021; A61B 5/256; A61B 5/318; A61B 5/6801; A61B 5/6814; A61B 5/369

See application file for complete search history.

(56) References Cited

U.S. PATENT DOCUMENTS

| | | | |
|---|---|---|---|
| 6,433,055 | B1 | 8/2002 | Kleyer et al. |
| 8,784,293 | B2 | 7/2014 | Berka et al. |
| 8,932,199 | B2 | 1/2015 | Berka et al. |
| 10,456,058 | B2 | 10/2019 | Lukoschek et al. |
| 11,122,982 | B2 | 9/2021 | Wang et al. |
| 11,553,870 | B2 | 1/2023 | Le et al. |
| 11,638,551 | B2 | 5/2023 | Elwood et al. |
| 11,684,303 | B2 | 6/2023 | Pyrzowski et al. |
| 11,786,167 | B2 | 10/2023 | Elwood et al. |
| 12,236,014 | B2 | 2/2025 | Yeo et al. |

(Continued)

FOREIGN PATENT DOCUMENTS

| | | |
|---|---|---|
| CN | 106223112 A | 12/2016 |
| CN | 106947427 A | 7/2017 |

(Continued)

OTHER PUBLICATIONS

Combined Search and Examination Report from corresponding Great Britain application No. 2316544.2 dated Apr. 30, 2024.

(Continued)

*Primary Examiner* — Jeffrey G. Hoekstra
(74) *Attorney, Agent, or Firm* — Goodwin Procter LLP

(57) ABSTRACT

Broadly speaking, embodiments of the present techniques provide a skin-conformable and compact wearable electronic apparatus for monitoring physiological and/or brain signals of the wearer.

19 Claims, 6 Drawing Sheets

(56) References Cited

U.S. PATENT DOCUMENTS

| | | | | |
|---|---|---|---|---|
| 2007/0249952 | A1* | 10/2007 | Rubin | G04G 15/003 600/544 |
| 2008/0091090 | A1* | 4/2008 | Guillory | A61B 5/6814 600/301 |
| 2011/0230749 | A1 | 9/2011 | Chan et al. | |
| 2013/0041235 | A1* | 2/2013 | Rogers | A61N 1/05 600/386 |
| 2015/0087921 | A1 | 3/2015 | Felix et al. | |
| 2016/0113544 | A1 | 4/2016 | Li et al. | |
| 2017/0258358 | A1 | 9/2017 | Bishay et al. | |
| 2018/0116546 | A1 | 5/2018 | Pastoor et al. | |
| 2019/0200925 | A1 | 7/2019 | Aimone et al. | |
| 2019/0387990 | A1 | 12/2019 | Hatakeyama et al. | |
| 2020/0375537 | A1 | 12/2020 | Carlile et al. | |
| 2025/0045565 | A1 | 2/2025 | Emami Gohari et al. | |

FOREIGN PATENT DOCUMENTS

| | | | | |
|---|---|---|---|---|
| CN | 107915997 | A | 4/2018 | |
| CN | 108943307 | A | 12/2018 | |
| CN | 111253751 | A | 6/2020 | |
| CN | 113192868 | A | 7/2021 | |
| CN | 114990889 | A | 9/2022 | |
| EP | 0392262 | A2 | 10/1990 | |
| EP | 0558045 | A1 | 9/1993 | |
| EP | 1451873 | A2 | 9/2004 | |
| EP | 3578096 | A1 | 12/2019 | |
| EP | 4245796 | A1 | 9/2023 | |
| JP | 2018174995 | A | 11/2018 | |
| KR | 20160015419 | A | 2/2016 | |
| WO | WO-0059374 | A1 * | 10/2000 | A61B 5/14553 |
| WO | 2003065926 | A2 | 8/2003 | |
| WO | WO-2011076886 | A2 * | 6/2011 | A61B 5/02028 |
| WO | WO-2014039525 | A1 * | 3/2014 | A61B 5/282 |
| WO | WO-2015061282 | A1 * | 4/2015 | A61B 5/25 |
| WO | 2016144043 | A1 | 9/2016 | |
| WO | WO-2017041014 | A1 * | 3/2017 | A61B 5/0006 |
| WO | WO-2019077120 | A1 * | 4/2019 | A61B 5/7264 |

OTHER PUBLICATIONS

Combined Search and Examination Report from corresponding Great Britain application No. 2316545.9 dated Apr. 30, 2024.

Jeong S.H et al., PDMS-Based Elastomer Turned Soft, Stretchable and Sticky for Epidermal Electronics, Adv. Mater, 28, pp. 5830-5836, (2016).

Kim J. et al., Highly Conformable, Transparent Electrodes for Epidermal Electronics, Nano Letters, vol. 18, 25 pages, (2018).

Search Report from corresponding GB application No. 2415652.3 dated Feb. 26, 2025.

Supplementary Disclosures from corresponding GB application No. 2415652.3 dated Feb. 25, 2025.

Yuki Y., et al., Efficient Skin Temperature Sensor and Stable Gel-Less Stick ECG Sensor for Wearable Flexible Healthcare Patch, Adv. Healthcare Mater, 6, (2017).

Great Britain Search Report from corresponding Great Britain application No. 2415651.5 dated Mar. 18, 2025.

Debener, S., et al., Unobtrusive ambulatory EEG using a smartphone and flexible printed electrodes around the ear, Sci Rep, 5: 16743 (2015).

Eickenscheidt, M., et al., Highly Porous Platinum Electrodes for Dry Ear-EEG Measurements, Sensors, 20(11): 3176 (2020).

Kappel, S.L., et al., Dry-Contact Electrode Ear-EEG, IEEE Trans Biomed Eng, 66(1): 150-158 (2019).

OpenBCI, Open-EEGrid Kit, retrieved from https://shop.openbci.com/products/ceegrid?srsltid=AfmBOoqbYuatG0gYxBXpNEXfBTKWcw7DIKjZNa1GvLTHEdYEGaxpPtl1 in 2025.

Petrossian, G., et al., Advances in Electrode Materials for Scalp, Forehead, and Ear EEG: A Mini-Review, ACS Appl Bio Mater, 6(8): 3019-3032 (2023).

Tsouti, V., et al., Capacitive microsystems for biological sensing, Biosens Bioelectron, 27(1): 1-11 (2011).

Valentin, O., et al., Custom-Fitted In- and Around-the-Ear Sensors for Unobtrusive and On-the-Go EEG Acquisitions: Development and Validation, Sensors, 21(9): 2953 (2021).

Vaswani, A., et al., Attention Is All You Need, Adv Neural Inf Process Syst, 30: 5998-6008 (2017).

Velcescu, A., et al., Flexible 3D-Printed EEG Electrodes, Sensors, 19(7): 1650 (2019).

Wikipedia, Ear-EEG, retrieved from https://en.wikipedia.org/wiki/Ear-EEG on Dec. 11, 2025.

Xing, L., et al., 3D-printed, directly conductive and flexible electrodes for personalized electroencephalography, Sens Actuators A Phys, 349(1): 114062 (2023).

* cited by examiner

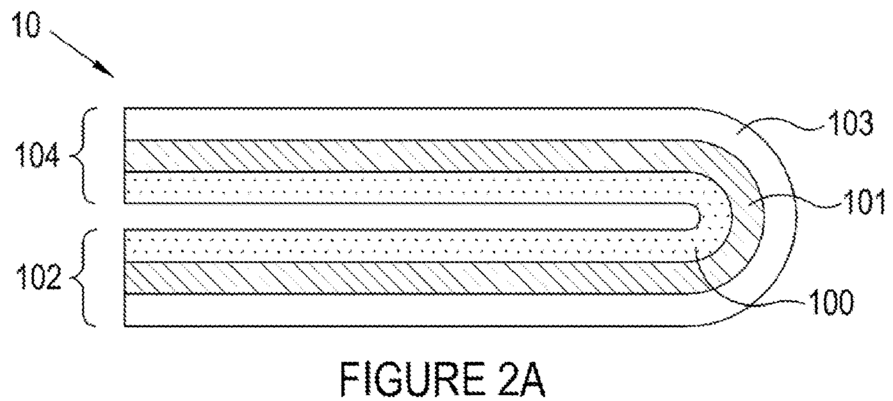
FIGURE 2A
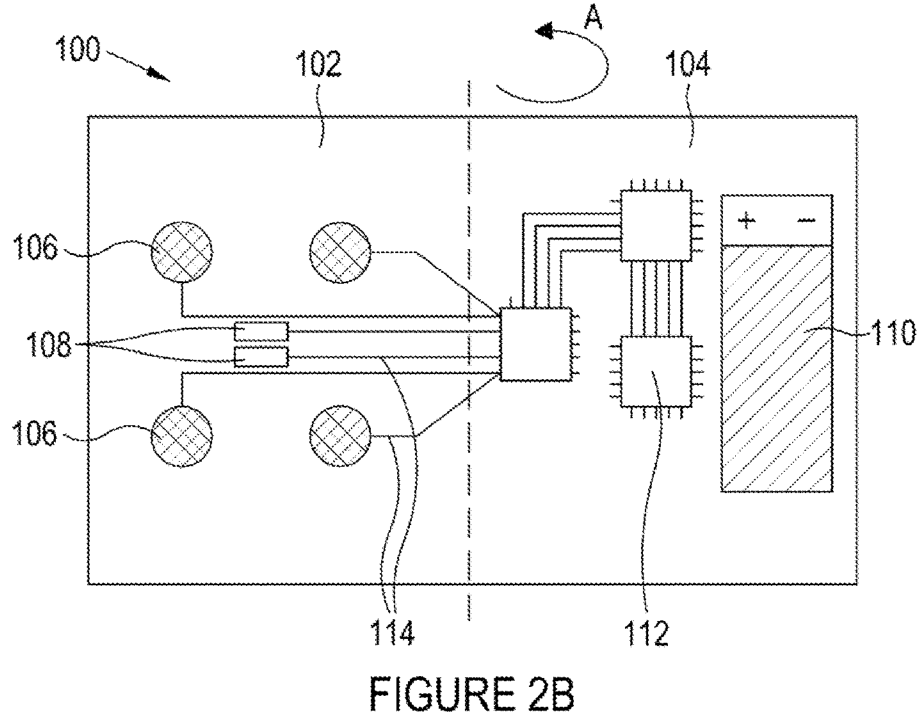
FIGURE 2B
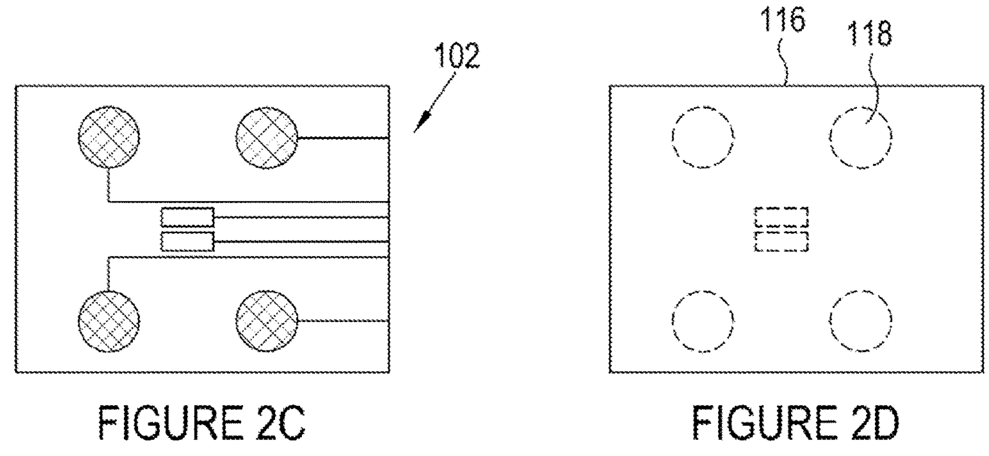
FIGURE 2C
FIGURE 2D

WEARABLE SENSOR

RELATED APPLICATIONS

This application claims priority to Great Britain Application No. 2116428.0 filed 15 Nov. 2021, the entire disclosure of which is being hereby incorporated by reference herein.

FIELD

The present techniques generally relate to a wearable sensor. In particular, the present techniques provide a skin-conformable and compact wearable electronic apparatus for monitoring physiological and/or brain signals of the wearer.

BACKGROUND

Good quality ambulatory brain recordings are difficult to obtain because current techniques for monitoring human brain activity non-invasively are extremely susceptible to motion artefacts. Although devices exist which enable the collection of brain data outside clinical or laboratory environments, these devices require their wearer to refrain from making any head or body movements in order to acquire interpretable data. As such, it is currently difficult—without resorting to surgery—to monitor human brain activity effectively during most human behaviours. Solving this problem would, for instance, enable patients with neurological conditions to be monitored remotely, without interfering with their daily lives.

The present applicant has therefore identified the need for an improved sensor for monitoring physiological and/or brain activity data of users.

SUMMARY

The present techniques provide a wearable electronic apparatus for monitoring physiological and/or brain signals, the apparatus comprising: at least one assembly of layers, the assembly comprising: a first flexible polymer thin film substrate layer, a second flexible polymer thin film passivation layer, and a conductive layer sandwiched between the first flexible polymer thin film layer and the second flexible polymer thin film layer, wherein the second flexible polymer thin film passivation layer shields the first flexible polymer thin film substrate layer and the conductive layer; at least one sensor for monitoring physiological and/or brain signals, provided on the conductive layer; and circuitry coupled to the at least one sensor, the circuitry comprising: a wireless communication module for transmitting sensor data to an external device, and at least one integrated circuit chip, wherein the conductive layer comprises a plurality of conductive tracks for coupling the at least one sensor to the at least one integrated circuit chip.

The second flexible polymer thin film passivation layer may comprise at least one opening that corresponds to a position of the at least one sensor, such that when the apparatus is attached to a user's skin, the at least one sensor is in contact with the skin.

The apparatus may further comprise an adhesive layer provided on the second flexible polymer thin film passivation layer. The adhesive layer may comprise at least one opening that corresponds to a position of the at least one sensor (and a position of the opening(s) of the passivation layer), such that when the apparatus is attached to a user's skin, the at least one sensor is in contact with the skin.

The first flexible polymer thin film layer and the second flexible polymer thin film passivation layer may each have a thickness of up to 10 microns. This may advantageously enable the layers to conform to the user's skin. In some cases, the thickness of the passivation layer and the material from which the passivation layer is formed may enable the passivation layer to adhere to the skin without requiring an additional adhesive layer.

The plurality of conductive tracks on the first flexible polymer thin film layer may be flexible. The plurality of conductive tracks on the first flexible polymer thin film layer may have a thickness of up to 2 microns, which enables the tracks to flex and conform to the user's skin.

In one example arrangement, the assembly of layers is folded to form a first portion and a second portion, and wherein the at least one sensor is provided in the first portion of the assembly of layers and the circuitry is provided in the second portion of the assembly of layers. This is advantageous because it enables all the sensing, circuitry and electrical components of the apparatus to be provided on a single substrate layer, which may make manufacturing simpler. Folding the assembly of layers enables the area of the apparatus to be reduced, which makes the apparatus more suitable for wearing by a user, and may enable the apparatus to be worn in a discrete manner.

The assembly of layers may comprise a single fold. For example, the assembly of layers may be folded in half.

Alternatively, the assembly of layers may comprise two or more folds.

In another example arrangement, the apparatus may comprise a first assembly of layers and a second assembly of layers, wherein the first and second assembly of layers are stacked. As explained in more detail below, the at least one sensor may be provided on the conductive layer of the first assembly of layers, and the circuitry may be provided on the conductive layer of the second assembly of layers.

In a yet further example arrangement, the apparatus further comprises a rigid printed circuit board and a flexible cable for electrically connecting the assembly of layers to the rigid printed circuit board. In this arrangement, the sensing and readout components of the apparatus may be separated such that sensing components (electrode and/or chip sensors and required conductive tracks and solder pads) are provided on a conductive layer of the assembly of layers, whereas readout components (integrated circuit chips comprising amplification, digitization, non-skin-contacting sensors, memory storage and wireless transmission functionalities) are provided on the rigid printed circuit board.

The readout board or rigid printed circuit board may be stacked on the first flexible polymer thin film layer to reduce the area/volume taken up by the device. The assembly of layers may be removeable. This may advantageously enable the assembly of layers to be replaced after wear and tear, or to be upgraded to provide additional functionality.

The at least one sensor may be any one or more of: an accelerometer; an electroencephalograph; an electromyograph; an electrocardiograph; a temperature sensor; a thermistor; a blood pressure monitor; a photoplethysmography sensor; a pulse oximeter; a galvanic skin response sensor; a biochemical sensor; a sweat biochemical sensor; and an electrodermal activity sensor. It will be understood that this is a non-exhaustive list of possible sensors.

The apparatus may further comprise a battery. The battery may be a rigid battery or may be a flexible battery.

The apparatus may further comprise an actuator. This may enable the apparatus to, for example, stimulate brain activity or otherwise apply energy to the user's body, and resulting brain activity or physiological signals may be measured by the at least one sensor. For example, the actuator may be an ultrasound transducer.

When the apparatus is provided on a user's head, the at least one sensor senses brain signals. In this case, the at least one sensor may be able to provide (directly or indirectly) information on the cognition, emotional state, peripheral nervous system state or disease indicators.

BRIEF DESCRIPTION OF THE DRAWINGS

Implementations of the present techniques will now be described, by way of example only, with reference to the accompanying drawings, in which:

FIG. 2A is a schematic cross-sectional view of the assembly of layers which forms part of a first example arrangement of an apparatus for monitoring physiological and/or brain signals;

FIG. 2B is a plan view of the first example arrangement of an apparatus for monitoring physiological and/or brain signals;

FIG. 2C is a view of a second flexible polymer thin film passivation layer of the apparatus of FIG. 2B;

FIG. 2D is a view of an adhesive layer which may form part of the apparatus of FIG. 2B;

DETAILED DESCRIPTION OF THE DRAWINGS

Figure 1:
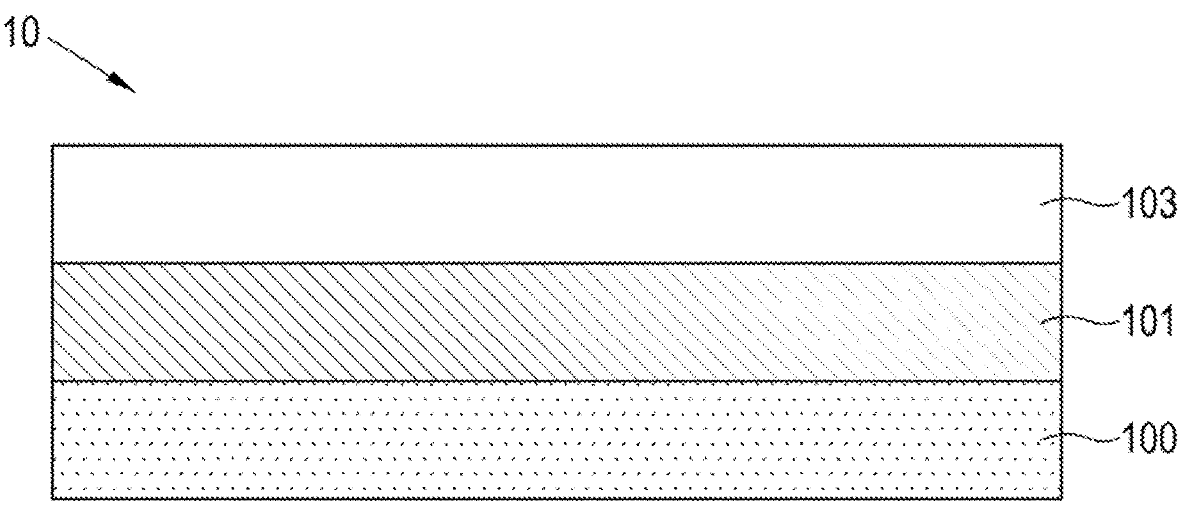
FIG. 1 is a schematic cross-sectional view of an assembly of layers which form part of an apparatus for monitoring physiological and/or brain signals.

Broadly speaking, embodiments of the present techniques provide a skin-conformable and compact wearable electronic apparatus for monitoring physiological and/or brain signals of the wearer.

Two causes of motion artefacts in electroencephalography are 1) displacement of sensors relative to the skin and/or interruption or alteration of the quality of electrical contact between the skin and the sensor, and 2) cable sway introducing electrical noise into analog signals.

The present techniques solve the problem by providing ultra-thin sensors on thin (e.g. up to 50 μm) polymer films, instead of using rigid materials to build the sensors. These thin sensors are able to conform to the skin's surface, establishing perfect contact with it. These thin sensors have extremely low mass, meaning by using an adhesive or another method of bonding them to the skin, they can remain in place even during vigorous movement.

The present techniques also provide a wearable apparatus that is miniaturised and so can be placed on a user's head (e.g., behind the ear, on the forehead or other hairless skin regions), which enables it to establish much better electrical contact with the skin than on hairy regions of the head.

The apparatus of the present techniques is advantageously not affected by cable sway. This is because circuits and connections between electrical elements of the apparatus are made through conductive tracks deposited onto the thin films themselves, which move with the skin. In contrast, existing devices have to use cables, which move relative to the skin and thus introduce motion artefacts into the signal.

In some versions of the apparatus, all the electrical circuits and chips are assembled onto skin-conformal thin-films, creating a fully autonomous sensor patch. In another version, only the sensors and their output conductive tracks are implemented on thin films; the remaining electronics are assembled onto a miniature multi-layer rigid PCB which interfaces with the thin-film sensor module through an extension of the thin film patterned into a cable. These different versions are now described with reference to the drawings.

In each version of the wearable electronic apparatus, the apparatus comprises: at least one assembly of layers, the assembly comprising: a first flexible polymer thin film substrate layer, a second flexible polymer thin film passivation layer, and an electrically conductive layer sandwiched between the first flexible polymer thin film layer and the second flexible polymer thin film layer, wherein the second flexible polymer thin film passivation layer shields the first flexible polymer thin film substrate layer and the conductive layer; at least one sensor for monitoring physiological and/or brain signals, provided on the conductive layer; and circuitry coupled to the at least one sensor, the circuitry comprising: a wireless communication module for transmitting sensor data to an external device, and at least one integrated circuit chip, wherein the conductive layer comprises a plurality of conductive tracks for coupling the at least one sensor to the at least one integrated circuit chip.

FIG. 1 is a schematic cross-sectional view of an assembly of layers 10 which forms part of an apparatus for monitoring physiological and/or brain signals. The assembly of layers 10 comprises a first flexible polymer thin film substrate layer 100, a second flexible polymer thin film passivation layer 103, and a conductive layer 101 sandwiched between the first flexible polymer thin film layer 100 and the second flexible polymer thin film layer 103. The conductive layer 101 is electrically conductive and may be formed of any suitable material, such as, but not limited to, a metal, metallic material, or metal alloy, for example. The passivation layer 103 shields the substrate layer 100 and the conductive layer 101 from electromagnetic interference and from the external environment. At least one assembly of layers 10 features in each of the three example arrangements of the apparatus described below. In some cases, an optional adhesive layer (not shown) may be provided on the passivation layer to enable the assembly of layers 10 (and therefore the wearable apparatus) to be adhered to skin. In some cases, an adhesive layer is not required as the passivation layer may itself be formed from a certain material with a certain thickness that may enable the layer to adhere to the skin.

Three example arrangements of an apparatus for monitoring physiological and/or brain signals, each comprising the assembly of layers shown in FIG. 1, are now described.

A first example arrangement of an apparatus for monitoring physiological and/or brain signals comprises an assembly of layers 10 that has been folded. The whole assembly 10 is folded to form two portions 102, 104. In use, portion 102 may be closer to the skin than portion 104. Folding the assembly of layers reduces the total area of the apparatus which may make the apparatus more discrete to wear and/or may enable the apparatus to be adhered to certain parts of the body, such as behind the ear or on the wrist. The apparatus may comprise an adhesive layer, which may be provided on portion 102 of the passivation layer 103.

FIG. 2B is a plan view of the assembly of layers of the first example arrangement of an apparatus for monitoring physiological and/or brain signals. In particular, FIG. 2B shows the first flexible polymer thin film substrate layer 100. The polymer thin film substrate layer 100 may have a thickness of up to 50 μm.

The assembly of layers 10 of the apparatus comprises a conductive layer 101. In this example, the conductive layer 101 comprises the circuitry and the at least one sensor of the apparatus. As shown in FIG. 2B, the conductive layer is deposited on a surface of the first flexible polymer thin film substrate layer 100. Here, the apparatus comprises at least one sensor 106, 108 for monitoring physiological and/or brain signals. In this case, the at least one sensor 106, 108 is also provided as part of the conductive layer. Thus, the sensors 106, 108 may take the form of conductive (e.g., metal) electrodes deposited on the surface of the first flexible polymer thin film substrate layer 100 and/or integrated circuit chips mounted onto structures provided as part of the same conductive layer. In FIG. 2A, four sensors 106 are shown, but it will be understood that this non-limiting and exemplary. Sensors 106 may be analog sensors which may be electrodes that are deposited on a surface of the polymer thin film substrate layer 100. The apparatus comprises at least one digital sensor 108 for monitoring and digitising measures of the user's physiology or of the environment. Sensors 108 may be surface-mounted onto conductive metal pads deposited on the polymer thin film substrate layer 100.

In this example arrangement, the assembly of layers comprises a second flexible polymer thin film passivation layer 103 (shown in FIG. 2A, but not shown in FIG. 2B). The passivation layer 103 shields the substrate layer 100 and the conductive layer (and circuitry thereof). The passivation layer 103 may be configured to conform to skin.

The apparatus comprises circuitry coupled to the at least one sensor 106, 108. The circuitry comprises a wireless communication module for transmitting sensor data to an external device. The circuitry comprises at least one integrated circuit chip 112. In this example, three integrated circuit, IC, chips 112 are shown, but it will be understood this is non-limiting and merely exemplary. The at least one IC chip 112 may be an amplifier, an analog-digital converter, a memory, a micro-controller unit, and/or a sensor which does not require skin contact (such as accelerometers, gyroscopes, or barometers for example). In some cases, the wireless communication module may be provided as an IC chip 112. A single IC chip may serve more than one function. For example, a micro-controller unit chip may be used which also has wireless communication module functionalities.

The apparatus comprises a flexible or thin profile battery 110 which is surface-mounted onto one of the polymer thin-films of the assembly to power the at least one IC chip 112.

As mentioned above, the conductive layer 101 of the apparatus comprises a plurality of conductive tracks 114 for coupling the at least one sensor 106, 108 to the at least one integrated circuit chip 112 and flexible battery 110. The conductive tracks or traces may be deposited on the surface of the first polymer thin film substrate layer 100. The conductive layer, and thus the conductive tracks 114, may be up to 1 μm in thickness (height), and may be deposited or printed directly on the skin-conformal thin film 100. Thus, the conductive tracks 114 are themselves skin-conformal and follow the skin perfectly, avoiding movement-induced signal distortions.

It can be seen from FIG. 2B that the at least one sensor 106, 108 is provided on a first portion 102 of the flexible polymer thin film substrate layer 100 (and therefore on a first portion of the assembly of layers 10), and the circuitry (e.g. chips 112 and battery 110) is provided on a second portion 104 of the flexible polymer thin film substrate layer 100 (and therefore on a second portion of the assembly of layers 10). The whole assembly of layers 10, including the flexible polymer thin film substrate layer 100, is folded along the dashed line, as indicated by arrow A, to provide the folded structure shown in FIG. 2A. In use, when the apparatus is adhered to the skin of a user, the first portion 102 of the assembly of layers is closest to the skin and the second portion 104 of the assembly of layers is positioned further away from the skin.

FIG. 2C is a view of the first portion 102 of the first flexible polymer thin film layer 100 and the conductive layer 101 of the apparatus of FIG. 2A, which is formed when the assembly of layers 10 is folded. (The second flexible polymer thin film layer 103 is not shown here). The second flexible polymer thin film layer 103 of the assembly of layers 10 may comprise at least one opening that corresponds to a position of the at least one sensor 106, 108, such that when the apparatus is attached to a user's skin, the at least one sensor 106, 108 is in contact with the skin. Thus, the second flexible polymer thin film layer protects/shields certain components of the conductive layer (e.g., IC chip(s), conductive tracks, etc.), while exposing the at least one sensor 106, 108.

FIG. 2D is a view of an adhesive layer 116 which may form part of the apparatus of FIG. 2A. The adhesive layer 116 may be provided on a surface of the second flexible polymer thin film layer 103. The adhesive layer 116 may comprise at least one opening 118 that corresponds to a position of the at least one sensor 106, 108, such that when the apparatus is attached to a user's skin, the at least one sensor 106, 108 is in contact with the skin. The adhesive layer 116 may be a double-sided adhesive layer in order to stick both to the skin of the user and to the assembly of layers of the apparatus.

Figure 2E:
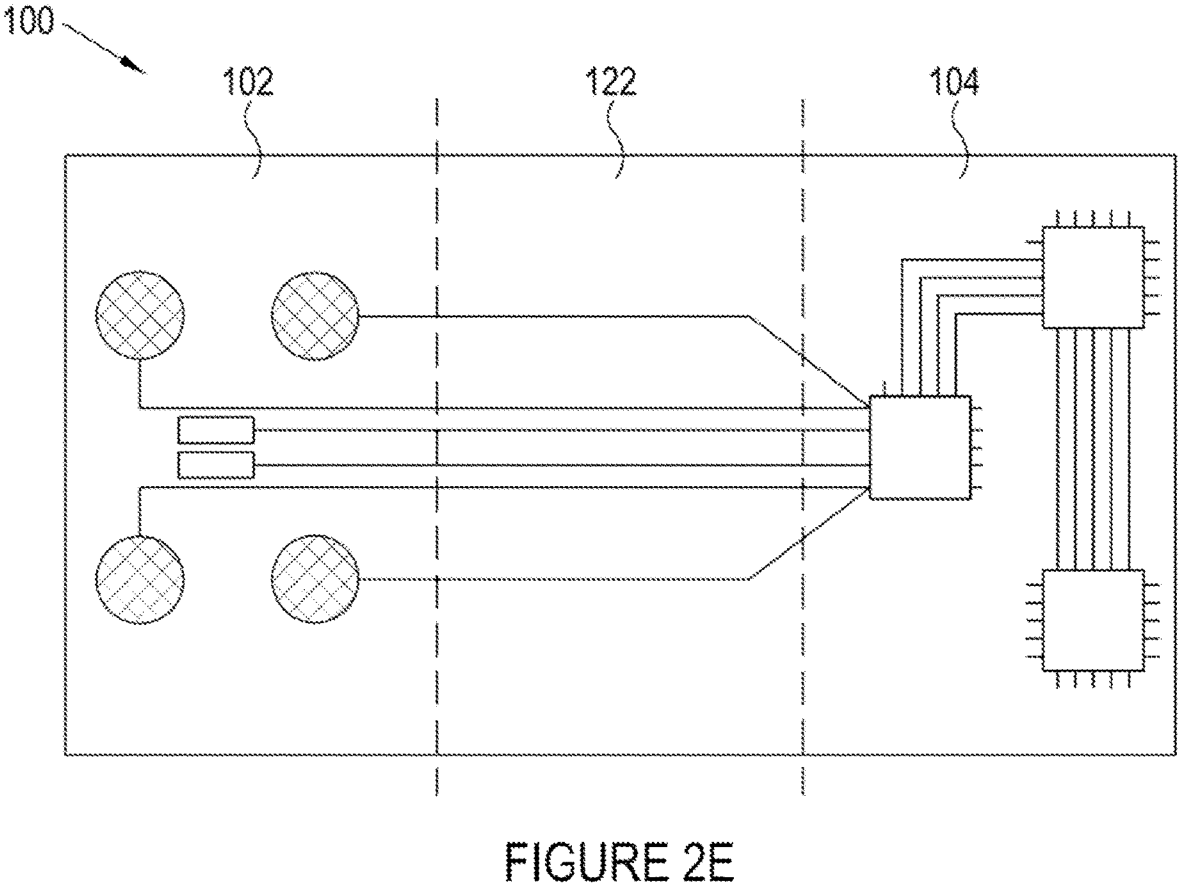
FIG. 2E is a plan view of the first example arrangement of FIG. 2B with two fold lines.

In FIGS. 2A and 2B, the flexible polymer thin film substrate layer 100 (and therefore the assembly of layers 10) comprises a single fold. The flexible polymer thin film 100 (and assembly of layers 10) may comprise two or more folds. FIG. 2E is a plan view of the first example arrangement of FIG. 2B with two fold lines. Here, a further portion 122 is formed by the two fold lines.

In the first example arrangement, the apparatus comprises a single assembly of layers 10. Another example arrangement is now described which has multiple stacked assemblies of layers.

Figure 3A:
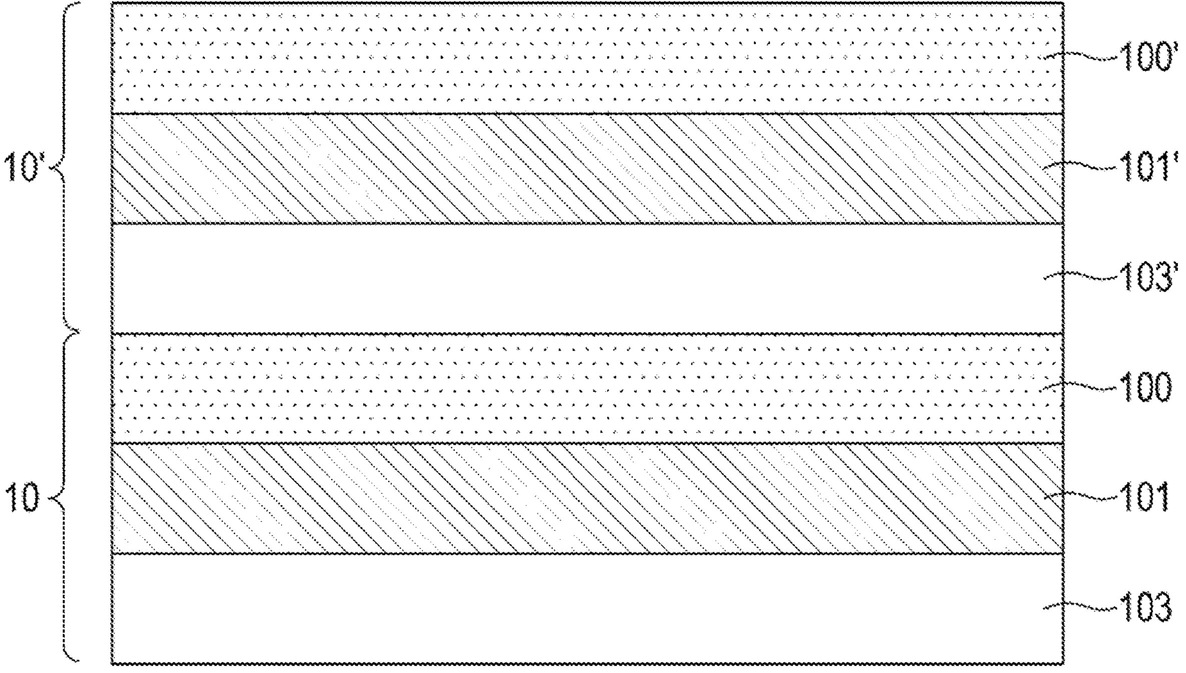
FIG. 3A is a schematic cross-sectional view of the assemblies of layers which form part of a second example arrangement of an apparatus for monitoring physiological and/or brain signals.

FIG. 3A is a schematic cross-sectional view of the assemblies of layers which form part of a second example arrangement of an apparatus for monitoring physiological and/or brain signals. It can be seen that in this example arrangement, there are two stacked assemblies of layers 10, 10'. It will be understood that an apparatus may be formed of more than two assemblies of layers, and that there may be additional layers provided in the stack including between the assemblies.

In this example, a first assembly of layers 10 comprises a first passivation layer 103 and a first substrate layer 100, with a first conductive layer 101 provided therebetween, and a second assembly of layers 10' comprises a second passivation layer 103' and a second substrate layer 100', with a second conductive layer 101' provided therebetween. In use, the first passivation layer 103 may be closest to the skin of a user and the second substrate layer 100' may be furthest from the skin. The apparatus may comprise an adhesive layer (not shown here) which may be provided on the first passivation layer 103.

Figure 3B:
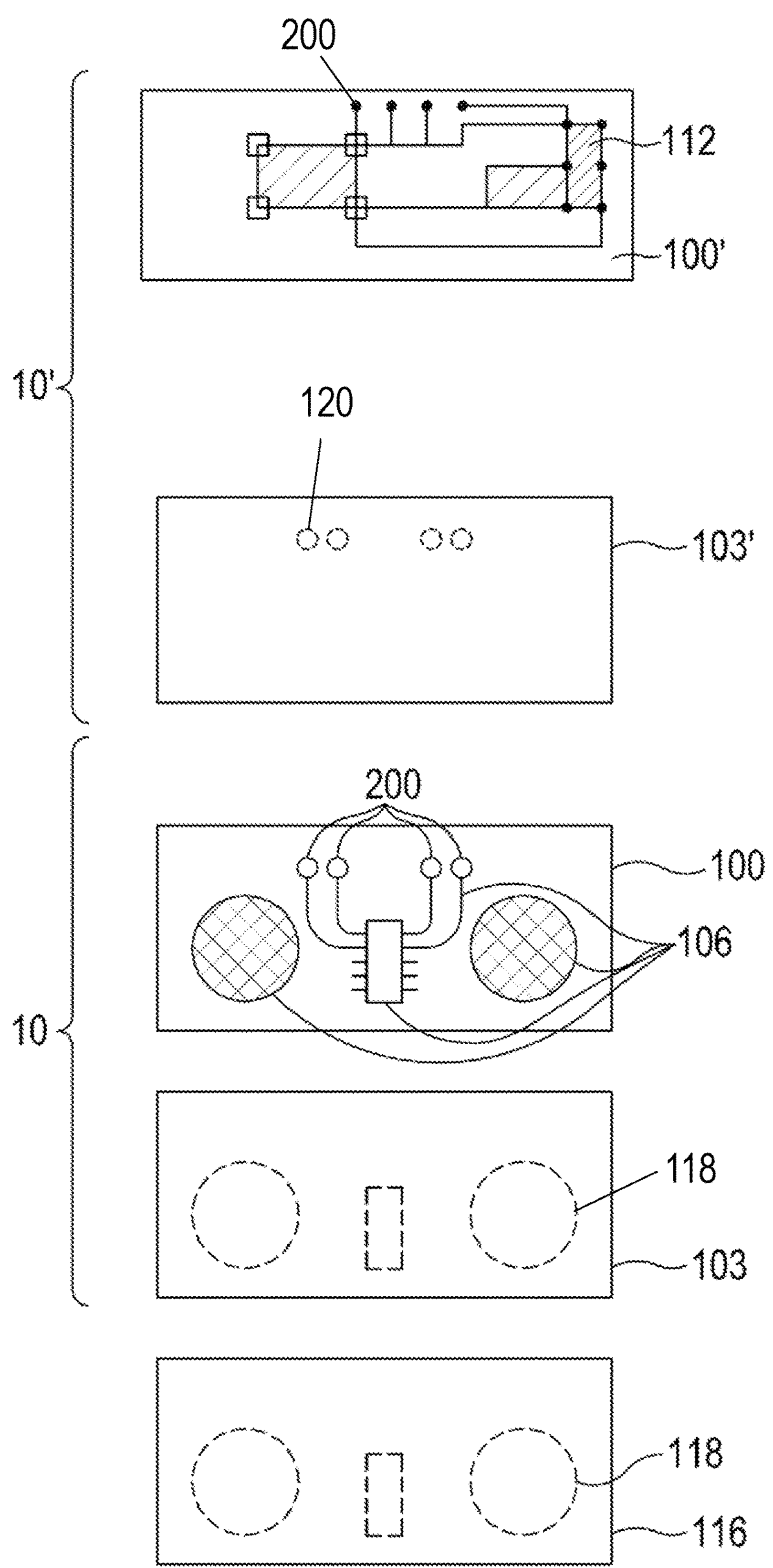
FIG. 3B is a schematic view of the second example arrangement of an apparatus for monitoring physiological and/or brain signals.

FIG. 3B is a schematic view of the second example arrangement of an apparatus for monitoring physiological and/or brain signals, showing the assemblies of layers 10, 10' in more detail.

The first assembly of layers 10 comprises the first substrate layer 100, which may be a flexible polymer thin film. The first assembly of layers 10 comprises the first conductive layer 101 (not shown in FIG. 3B) which may be provided on the first substrate layer 100. The first conductive layer 101 may comprise conductive tracks, at least one sensor 106 and conductive/metal pads 200 on which sensor chips 108 may be mounted. The first assembly of layers comprises the first passivation layer 103 for insulating and protecting the other layers, circuits, and components of the first assembly of layers 10. The first passivation layer 103 may be a flexible thin film polymer. The first passivation layer 103 may comprise one or more openings 118 which allow sensors of the first conductive layer 101 (on the first substrate layer 100) to contact the skin.

The second assembly of layers 10' comprises a second substrate layer 100' (which may be a flexible thin film polymer layer), and a second conductive layer 101' which is provided on the second substrate layer 100'. The second conductive layer 101' (not shown in FIG. 3B) may comprise conductive tracks, pads for mounting the at least one IC chip, and the at least one IC chip 112. The second assembly of layers comprises a passivation layer 103', and the second assembly of layers 10' is constructed so that the conductive layer 101' faces towards the passivation layer 103'. The second passivation layer 103' may be considered an "inner" passivation layer as it is provided within the stack of layers formed by stacking the two assemblies 10, 10'. The second passivation layer 103' may be a flexible thin film polymer, and may insulate the circuits and components of the first and second conductive layers 101, 101'. Communication and electrical contact between the conductive layers 101, 101' may be made through vias 120 which are formed in the substrate layer 100, 100' and inner passivation layer 103'. The vias 120 may be filled with conductive material (e.g., metal).

A flexible battery (not shown) may be mounted on top of the second thin film substrate layer 100'.

Figure 4A:
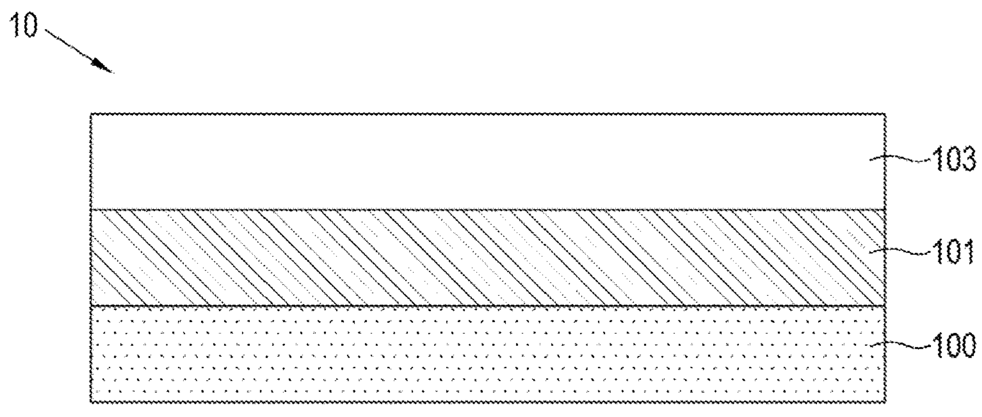
FIG. 4A is a schematic cross-sectional view of the assembly of layers which forms part of a third example arrangement of an apparatus for monitoring physiological and/or brain signals.

FIG. 4A is a schematic cross-sectional view of the assembly of layers which forms part of a third example arrangement of an apparatus for monitoring physiological and/or brain signals. In this example, the assembly 10 comprises a first flexible polymer thin film substrate layer 100, a second flexible polymer thin film passivation layer 103, and a conductive layer 101 sandwiched between the first flexible polymer thin film layer 100 and the second flexible polymer thin film layer 103. The assembly 10 may be flexible and may conform to the skin. In this example, the conductive layer 101 may comprise the at least one sensor, and, as explained below, readout components (e.g., the IC chip(s)) may be provided on a separate rigid circuit board which is electrically connected to the assembly 10.

Figure 4B:
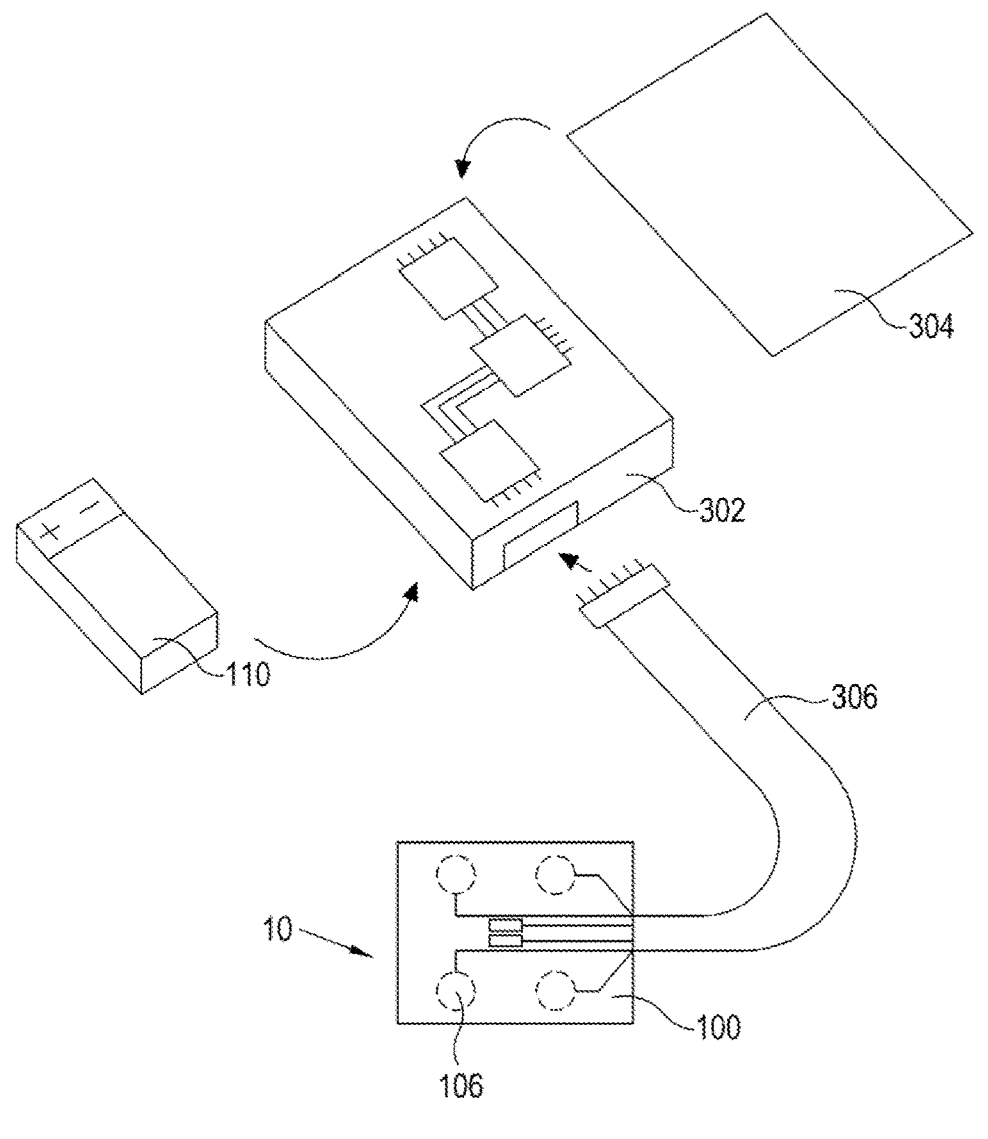
FIG. 4B is a schematic view of the third example arrangement of an apparatus for monitoring physiological and/or brain signals.

FIG. 4B is a schematic view of the third example arrangement of an apparatus for monitoring physiological and/or brain signals. In this arrangement, the at least one sensor 106 is provided on a first flexible polymer thin film substrate layer 100 of the assembly, while the circuitry is provided on a rigid printed circuit board, PCB, 302. The at least one IC chip 112 is provided on PCB 302. An analog front-end chip or other components of the circuitry that are highly sensitive to noise may be shielded with a miniature Faraday cage. The apparatus further comprises a flexible cable 306 for electrically connecting the assembly 10 to the rigid printed circuit board 302. The rigid printed circuit board 302 is stacked on the assembly 10. The assembly 10 may be removeable.

This arrangement of the apparatus comprises a battery 110, which may be mounted onto the underside of the rigid PCB 302 as indicated by the arrow in FIG. 4B, such that the battery 110 is located between PCB 302 and the assembly 10. The apparatus may comprise another flexible polymer thin film layer 304 to encapsulate the circuitry/rigid PCB 302.

In each of the arrangements described above, the circuitry may comprise: an analog front-end chip or combination of operational amplifier and ADC chips; a micro-controller unit; a wireless data transmission and reception chip and corresponding antenna; a memory storage in the form of an SD card or memory chip; and additional sensors which do not require skin contact.

The at least one sensor may comprise brain sensors (EEG) and a range of other surface physiology sensors. The at least one sensor is any one or more of: an accelerometer; an electroencephalograph; an electromyograph; an electrocardiograph; a temperature sensor; a thermistor; a blood pressure monitor; a photoplethysmography sensor; a pulse oximeter; a galvanic skin response sensor; a biochemical sensor; a sweat biochemical sensor; and an electrodermal activity sensor. The electroencephalogram and galvanic skin response sensor may be provided using deposited metal electrodes. The electrophysiological sensors (electrodes) which can be used for EEG, ECG and/or EMG measurements (which are the sensors most susceptible to motion-induced noise) or any other surface electrical signal from the body may be directly printed or deposited onto the thin film on which the sensors are provided, forming a patterned metal layer. The fabrication technique combined with the fact that the electrodes are up to 1 μm thick, means that the electrodes themselves are skin-conformal and not just flexible.

As explained above, all sensors in the apparatus may be assembled onto a polymer thin film (up to 50 μm thick, preferably between 1-10 μm thick), which is so thin it conforms to the skin. This enhances the sensor's ability to remain in contact with the skin during movement and to achieve a much better level of contact than a rigid sensor would be capable of, by following and adapting closely to the skin.

As mentioned above, all arrangements of the apparatus eliminate cables as a means of connection between sensors and readout electronics. In each arrangement, signals are transmitted from sensors to readout electronics by conductive tracks which are laid onto the thin film(s), and therefore move in tandem with the skin. This prevents distortion getting introduced into the signals by disruption of interconnects.

The apparatus may be designed specifically for hairless regions of the scalp where the advantage of thin films in adhering and following the skin closely is largest.

Adhesion to the skin may, in some cases, be provided by a double-sided adhesive with openings at the sensor sites to allow them to contact the skin.

As mentioned above, the apparatus wirelessly transmits data to a mobile, desktop or cloud computing platform for further data processing and extraction of insights relating to the cognitive and physiological state of the user.

The apparatus may further comprise an actuator. This may enable the apparatus to, for example, stimulate brain activity or otherwise apply energy to the user's body, and resulting brain activity or physiological signals may be measured by the at least one sensor. For example, the actuator may be an ultrasound transducer.

The polymer thin films may be formed from any suitable polymer, such as polyimide or parylene. These materials may have intrinsic characteristics or properties which help them to conform to, and even potentially adhere to, the skin.

The sensors and the circuitry may preferably be in close proximity. For example, the conductive tracks connecting the sensors to the circuitry may be no longer than 5 cm in length in each of the arrangements described above, which minimises the pick-up of distortions by analog signals.

Those skilled in the art will appreciate that while the foregoing has described what is considered to be the best mode and where appropriate other modes of performing present techniques, the present techniques should not be limited to the specific configurations and methods disclosed in this description of the preferred embodiment. Those skilled in the art will recognise that present techniques have a broad range of applications, and that the embodiments may take a wide range of modifications without departing from any inventive concept as defined in the appended claims.

What is claimed is:

1. A wearable electronic apparatus for monitoring physiological and/or brain signals, the apparatus comprising:

at least one assembly of layers, the assembly comprising:

a first flexible polymer thin film substrate layer, a second flexible polymer thin film passivation layer comprising at least one opening, and a conductive layer sandwiched between the first flexible polymer thin film substrate layer and the second flexible polymer thin film passivation layer, wherein the second flexible polymer thin film passivation layer shields the first flexible polymer thin film substrate layer and the conductive layer from electromagnetic interference;

at least one sensor for monitoring physiological and/or brain signals, provided on the conductive layer, wherein the at least one opening corresponds to a position of the at least one sensor, such that when the apparatus is configured to be attached to a user's skin, the at least one sensor is in contact with the user's skin; and circuitry coupled to the at least one sensor, the circuitry comprising:

a wireless communication module for transmitting sensor data to an external device, and at least one integrated circuit chip, wherein the conductive layer comprises a plurality of conductive tracks for coupling the at least one sensor to the at least one integrated circuit chip.

2. The apparatus as claimed in claim 1 further comprising an adhesive layer provided on the second flexible polymer thin film passivation layer, wherein the adhesive layer comprises at least one opening that corresponds to the position of the at least one sensor, such that when the apparatus is attached to the user's skin, the at least one sensor is in contact with the user's skin.

3. The apparatus as claimed in claim 1 wherein the first flexible polymer thin film substrate layer and the second flexible polymer thin film passivation layer each have a thickness of up to 10 microns.

4. The apparatus as claimed in claim 1 wherein the plurality of conductive tracks on the first flexible polymer thin film substrate layer are flexible.

5. The apparatus as claimed in claim 4 wherein the plurality of conductive tracks on the first flexible polymer thin film substrate layer have a thickness of up to 2 microns.

6. The apparatus as claimed in claim 1 wherein the assembly of layers is folded to form a first portion and a second portion, and wherein the at least one sensor is provided in the first portion of the assembly of layers and the circuitry is provided in the second portion of the assembly of layers.

7. The apparatus as claimed in claim 6 wherein the assembly of layers comprises a single fold.

8. The apparatus as claimed in claim 6 wherein the assembly of layers comprises two or more folds.

9. The apparatus as claimed in claim 1 wherein the apparatus comprises a first assemblies of layers and a second assembly of layers, wherein the first and second assemblies of layers are stacked.

10. The apparatus as claimed in claim 1 further comprising a rigid printed circuit board, and a flexible cable for electrically connecting the assembly of layers to the rigid printed circuit board.

11. The apparatus as claimed in claim 10 wherein the at least one sensor is provided in the assembly of layers, and the circuitry is provided on the rigid printed circuit board.

12. The apparatus as claimed in claim 10 wherein the rigid printed circuit board is stacked on the assembly of layers.

13. The apparatus as claimed in claim 10 wherein the assembly of layers is removeable.

14. The apparatus as claimed in claim 1 wherein the at least one sensor is any one or more of: an accelerometer; an electroencephalograph; an electromyograph; an electrocardiograph; a temperature sensor; a thermistor; a blood pressure monitor; a photoplethysmography sensor; a pulse oximeter; a galvanic skin response sensor; a biochemical sensor; a sweat biochemical sensor; and an electrodermal activity sensor.

15. The apparatus as claimed in claim 1 further comprising a battery, wherein the battery is a flexible battery.

16. The apparatus as claimed in claim 1 further comprising an actuator.

17. The apparatus as claimed in claim 16 wherein the actuator is an ultrasound transducer.

18. The apparatus as claimed in claim 1, wherein when the apparatus is configured to be provided on a user's head, the at least one sensor senses brain signals.

19. The apparatus as claimed in claim 18, wherein the at least one sensor provides information on the cognition, emotional state, peripheral nervous system state or disease indicators of the user.

* * * * *